(12) United States Patent
Takeshita et al.

(10) Patent No.: US 9,500,613 B2
(45) Date of Patent: Nov. 22, 2016

(54) CHIP FOR MEASURING NUMBER OF MICROBE, AND APPARATUS FOR MEASURING NUMBER OF MICROBE USING THE SAME

(75) Inventors: Toshiaki Takeshita, Ehime (JP); Junichi Kita, Kagawa (JP);
(Continued)

(73) Assignee: PANASONIC HEALTHCARE HOLDINGS CO., LTD., Tokyo (JP)

(*) Notice: Subject to any disclaimer, the term of this patent is extended or adjusted under 35 U.S.C. 154(b) by 385 days.

(21) Appl. No.: 14/233,251

(22) PCT Filed: Jul. 26, 2012

(86) PCT No.: PCT/JP2012/004761
§ 371 (c)(1),
(2), (4) Date: Jan. 16, 2014

(87) PCT Pub. No.: WO2013/021566
PCT Pub. Date: Feb. 14, 2013

(65) Prior Publication Data
US 2014/0150537 A1 Jun. 5, 2014

(30) Foreign Application Priority Data

Aug. 5, 2011 (JP) .................................. 2011-171578
Mar. 5, 2012 (JP) .................................. 2012-047635
May 10, 2012 (JP) .................................. 2012-108262

(51) Int. Cl.
*G01N 27/02* (2006.01)
*G01N 33/487* (2006.01)
(Continued)

(52) U.S. Cl.
CPC .............. *G01N 27/02* (2013.01); *C12M 41/36* (2013.01); *G01N 15/0656* (2013.01);
(Continued)

(58) Field of Classification Search
None
See application file for complete search history.

(56) References Cited

U.S. PATENT DOCUMENTS

| 4,719,441 | A | * | 1/1988 | Horn | ...................... G01N 27/07 29/611 |
| 4,833,413 | A | * | 5/1989 | Head | ...................... G01N 27/07 324/444 |

(Continued)

FOREIGN PATENT DOCUMENTS

| CN | 101278835 | 10/2008 |
| CN | 102053110 | 5/2011 |

(Continued)

OTHER PUBLICATIONS

Office Action issued Mar. 29, 2016 in European Application No. 12 822 097.7.
(Continued)

*Primary Examiner* — Paul West
*Assistant Examiner* — Mark A Shabman
(74) *Attorney, Agent, or Firm* — Wenderoth, Lind & Ponack, L.L.P.

(57) ABSTRACT

A chip that measures a number of microbes includes a chip main body in the form of a long plate, and a measuring electrode provided on a first end side in the longitudinal direction of the surface of the chip main body and that is immersed in a measurement liquid. A connecting electrode is connected to the measuring electrode and is provided on a second end side in the longitudinal direction of the surface of the chip main body. Ground electrodes are provided on the second end side in the longitudinal direction of the surface of the chip main body. Conductive patterns provided to the outer peripheral portion of the measuring electrode are connected to the ground electrodes.

12 Claims, 12 Drawing Sheets

(75) Inventors: Hidenori Morita, Ehime (JP);
Kazufumi Oouchi, Tokushima (JP)

(51) Int. Cl.
*G01N 15/06* (2006.01)
*C12M 1/34* (2006.01)
*G01N 15/00* (2006.01)
*G01N 35/00* (2006.01)

(52) U.S. Cl.
CPC . *G01N 33/48735* (2013.01); *G01N 2015/0065* (2013.01); *G01N 2035/00495* (2013.01)

(56) References Cited

U.S. PATENT DOCUMENTS

| | | | |
|---|---|---|---|
| 5,989,398 A * | 11/1999 | Young | G01N 25/30 204/408 |
| 6,247,350 B1 | 6/2001 | Tsukuda et al. | |
| 6,365,036 B1 * | 4/2002 | Polikarpus | G01N 27/4075 204/424 |
| 6,573,734 B2 * | 6/2003 | He | G01R 27/22 324/696 |
| 7,204,130 B2 | 4/2007 | Koram et al. | |
| 7,629,127 B2 | 12/2009 | Hubscher | |
| 7,651,595 B2 | 1/2010 | Doi et al. | |
| 2005/0115308 A1 | 6/2005 | Koram et al. | |
| 2006/0166374 A1 | 7/2006 | Hubscher | |
| 2006/0243589 A1 * | 11/2006 | Doi | G01N 27/3272 204/403.01 |
| 2010/0068797 A1 | 3/2010 | Hubscher | |
| 2010/0193358 A1 | 8/2010 | Hamada | |
| 2011/0094881 A1 | 4/2011 | Watanabe | |
| 2012/0244606 A1 | 9/2012 | Takeshita | |

FOREIGN PATENT DOCUMENTS

| | | |
|---|---|---|
| EP | 2 315 012 A2 | 4/2011 |
| EP | 2 315 012 A3 | 6/2011 |
| EP | 2 381 250 A1 | 10/2011 |
| JP | 56-118662 | 9/1981 |
| JP | 2000-125846 | 5/2000 |
| JP | 2007-6858 | 1/2007 |
| JP | 2010-220507 | 10/2010 |
| WO | 2004/072632 | 8/2004 |
| WO | 2006/092323 A1 | 9/2006 |
| WO | 2009/037804 | 3/2009 |
| WO | 2011/074190 | 6/2011 |

OTHER PUBLICATIONS

Extended European Search Report issued Dec. 19, 2014 in European Application No. 12822097.7.
Chinese Office Action issued Jul. 30, 2014 in corresponding Chinese Patent Application No. 201280029543.5 (with English translation).
International Search Report issued Oct. 9, 2012 in International (PCT) Application No. PCT/JP2012/004761.

* cited by examiner

CHIP FOR MEASURING NUMBER OF MICROBE, AND APPARATUS FOR MEASURING NUMBER OF MICROBE USING THE SAME

TECHNICAL FIELD

The present invention relates to a chip for measuring number of microbe, and to an apparatus for measuring number of microbe in which this chip is used.

BACKGROUND ART

A conventional chip for measuring number of microbe was configured as follows.

With a conventional chip for measuring number of microbe, for example, microbes were collected using a cotton swab or other such microbe collection tool from inside the oral cavity, and this microbe collection tool was immersed in a liquid in a container from an opening in the upper face of the container. After this, the liquid in the container was stirred with a stirrer, and in this state the microbe count was measured with a measuring electrode provided inside the container (see Patent Literature 1, for example).

CITATION LIST

Patent Literature

Patent Literature 1: Japanese Laid-Open Patent Application 2010-220507

SUMMARY

With the above-mentioned conventional configuration, elution and measurement of the microbes can be performed in the container, which was considered an advantage because the size of the device itself could be extremely small.

However, a measuring electrode has to be integrally provided to the inner wall surface of the container used to perform such measurements. Moreover, the takeoff leads from this measuring electrode to the outside of the container have to be made watertight somehow, which drives up the production cost.

Therefore, it ends up being expensive to take a microbe count when this container is used.

In view of this, it is an object of the present invention to provide a chip for measuring number of microbe with which measurement costs can be cut.

To achieve the stated object, the chip for measuring number of microbe of the present invention comprises a chip main body in the form of a long plate, a measuring electrode, a connecting electrode, a ground electrode, and a conductive pattern. The measuring electrode is provided on a first end side in the longitudinal direction of the surface of the chip main body, and is immersed in a measurement liquid. The connecting electrode is connected to the measuring electrode and is provided on a second end side on the opposite side from the first end in the longitudinal direction of the surface of the chip main body. The ground electrode is provided on the second end side of the surface of the chip main body. The conductive pattern is connected to the ground electrode and is provided to the outer peripheral portion of the measuring electrode.

The apparatus for measuring number of microbe of the present invention makes use of the above-mentioned chip for measuring number of microbe, and comprises a container holder, a rotary driver, an electrode insertion portion, and a measurement section. The container holder holds a bottomed cylindrical container having an opening in its upper face, with the opening facing up. The rotary driver rotates the container held in the container holder along with a liquid stored inside, around the central axis of the container running in a substantially vertical direction. The electrode insertion portion inserts the chip for measuring number of microbe through the opening in the container held in the container holder, at a position inside the container that is closer to the inner wall side than the central axis, and a position that is a specific distance away from the inner wall surface. The measurement section measures microbes at the measurement electrode of the chip for measuring number of microbe inserted into the container by the electrode insertion portion.

Furthermore, the chip for measuring number of microbe of the present invention comprises a chip main body in the form of a long plate, a measuring electrode, a connecting electrode, a connector, and a cover. The measuring electrode is provided on the lower end side of the surface of the chip main body, is immersed in a measurement liquid, and has mutually opposing first and second measuring electrodes on the lower end side of the surface of the chip main body. The connecting electrode is provided on the upper end side of the surface of the chip main body, is connected to a measurement device, and has first and second connecting electrodes. The connector connects the measuring electrode and the connecting electrode at the surface of the chip main body, and has a first connector where the first measuring electrode and the first connecting electrode are connected between the upper and lower ends of the surface of the chip main body, and a second connector where the second measuring electrode and the second connecting electrode are connected between the upper and lower ends of the surface of the chip main body. The cover is provided so as to cover the surface of the first and second connectors between the upper and lower ends of the surface of the chip main body.

With the chip for measuring number of microbe of the present invention, a container having a simple bottomed cylindrical shape with an opening in its upper face can be used as the container, which means that the production cost of the container can be lowered, and measurement costs reduced.

Furthermore, with a conventional chip for measuring number of microbe, when the microbe count is taken, the user holds the chip for measuring number of microbe in his fingers and inserts it into the electrode insertion portion of the device, but sometimes the user would accidentally touch the measuring electrode on the chip for measuring number of microbe, and the measuring electrode ended up being damaged by static electricity from the user when being inserted into the device.

With the chip for measuring number of microbe of the present invention, since the conductive pattern is provided around the periphery of the measuring electrode, if the user accidentally touches the measuring electrode, he will also touch the conductive pattern at the same time, and static electricity from the user will flow through the conductive pattern to the device side. This prevents the measuring electrode from being damaged by static electricity. As a result, the user need not worry about the position where he holds the chip for measuring number of microbe (the position where he grasps the chip for measuring number of microbe), and this makes the chip for measuring number of microbe easier to handle.

With the chip for measuring number of microbe of the present invention, when the measuring electrode is immersed in a measurement liquid in order to take a microbe count, the lower parts of the first and second connectors connected to the measuring electrode are also immersed in the measurement liquid. Accordingly, when a specific voltage is applied to the measuring electrode during measurement, voltage is also applied to the immersed part of the connectors, and the immersed part has an impedance component. Furthermore, when the measurement liquid is rotated around the center axis of the container during measurement, the surface of the measurement liquid is shaken in the vertical direction, causing the immersed part of the connectors to fluctuate. This fluctuation creates variance in the impedance component of the immersed part, and variance occurs in the measurement value obtained when measurement was performed at a varying impedance. This results in lower measurement accuracy.

In view of this, with the chip for measuring number of microbe of the present invention, a cover that covers the surface of the first and second connectors is provided between the upper and lower ends of the surface of the chip main body, so the first and second connectors do not touch the surface of the measurement liquid, and no variance in the impedance component occurs in the first and second connectors. As a result, there is no variance in the measurement value, so measurement accuracy can be improved.

DETAILED DESCRIPTION

Embodiment 1

The measurement chip (chip for measuring number of microbe) 15 and apparatus for measuring number of microbe pertaining to an embodiment of the present invention will now be described through reference to the drawings.

Figure 1:
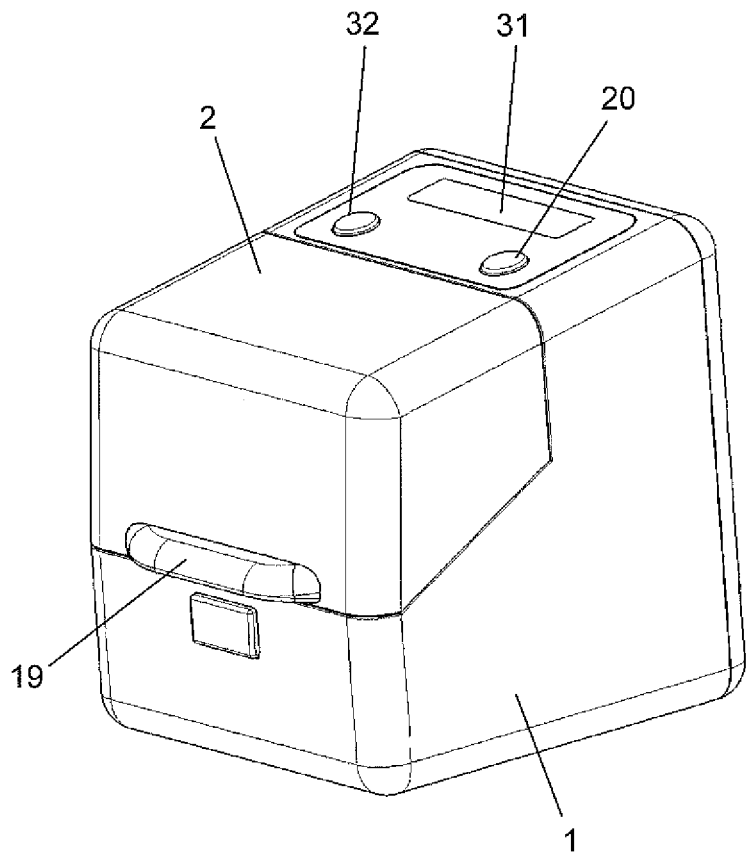
FIG. 1 is an oblique view of the apparatus for measuring number of microbe pertaining to an embodiment of the present invention.
Figure 2:
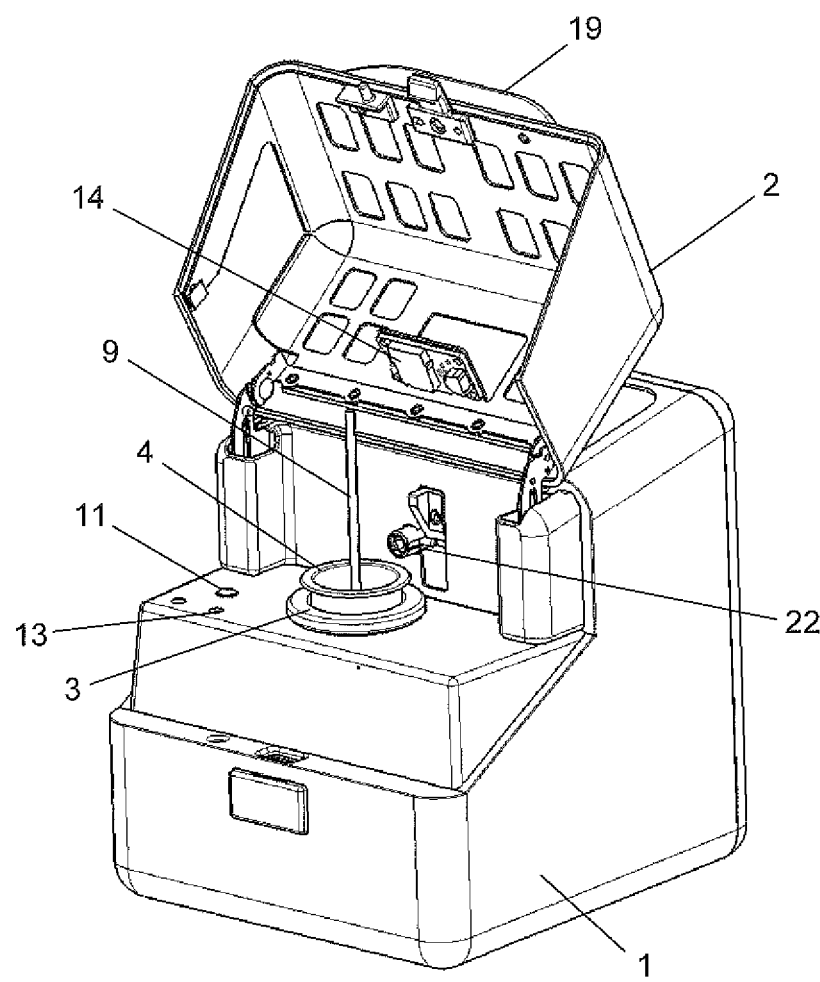
FIG. 2 is an oblique view of the operating state of the apparatus for measuring number of microbe in FIG. 1.

As shown in FIG. 1, the apparatus for measuring number of microbe in this embodiment comprises a box-shaped main body case 1 and a front cover 2 provided openably upward at the front (see FIG. 2).

As shown in FIG. 2, a container holder 3 that has opening at the top and holds a container 4 is provided to the rear side of the front cover 2 on the inside of the main body case 1.

Figure 3:
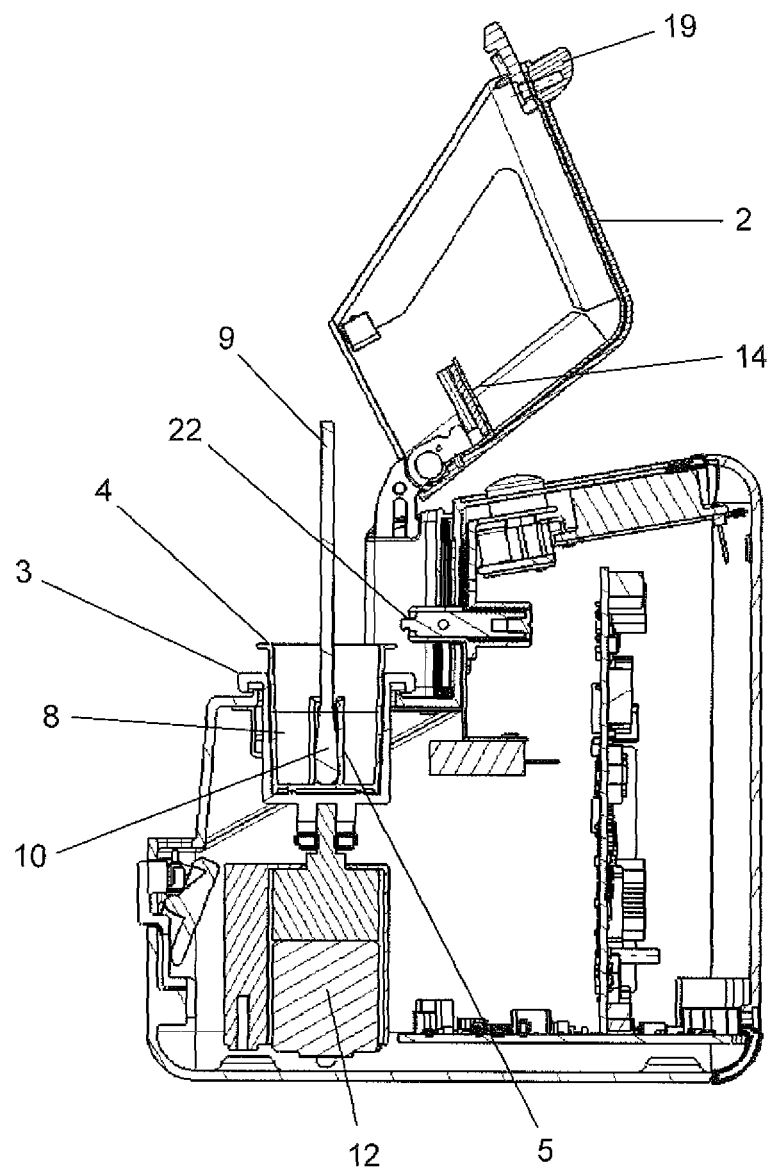
FIG. 3 is a cross section of the operating state of the apparatus for measuring number of microbe in FIG. 1.
Figure 4:
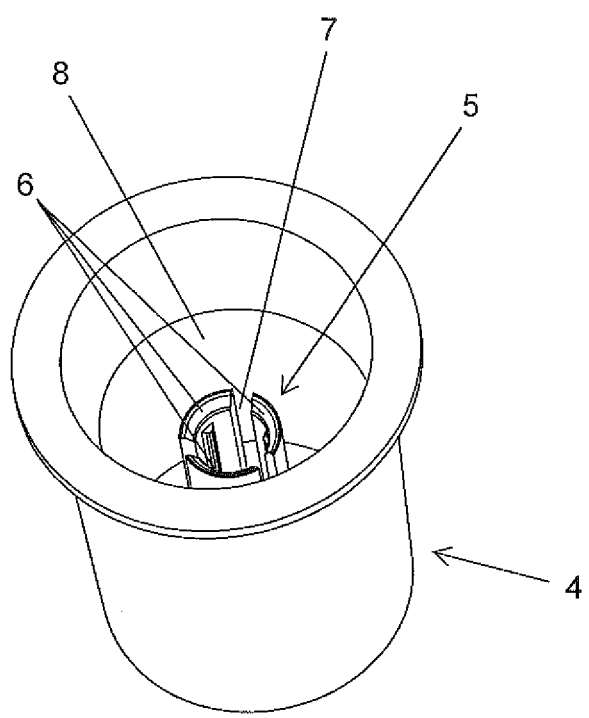
FIG. 4 is an oblique view of a container in the apparatus for measuring number of microbe in FIG. 1.

As shown in FIGS. 3 and 4, the container 4 is in the form of a bottomed cylinder having a circular opening at the top, and is held in the container holder 3 with the opening facing up. A cylindrical holder 5 is formed on the bottom face of the container 4. Three elution protrusions 6 are formed substantially vertically in the inner side face of the holder 5 at intervals of 120 degrees in the peripheral direction. Three elution grooves 7 that pass through from the inside to the outside are formed at intervals of 120 degrees in the side face of the holder 5. Further, pure water 8 (an example of a measurement liquid) for eluting microbes M (see FIG. 8) is held in the container 4.

As shown in FIG. 3, a collection portion 10 provided to the lower end of a rod-shaped microbe collection tool 9 is inserted from above into the holder 5 of the container 4, and the microbe collection tool 9 is held by the holder 5. The collection portion 10 of the microbe collection tool 9 is inserted into an oral cavity, for example, to pick up saliva and collect the microbes M.

In this state, the user presses the switch 11 in FIG. 2 with the left hand while grasping the upper end portion of the microbe collection tool 9 with the right hand, for example. The rotation of a motor 12 then causes the container holder 3 to rotate. Since drive protrusions (not shown) of the container holder 3 are engaged with engagement protrusions (not shown) of the container 4 at this point, the container 4 can be rotated. When the container 4 rotates, the operation lamp 13 in FIG. 2 is lit. In this state, the container 4 rotates for a preset timer time (such as 10 seconds).

This rotation causes the elution protrusions 6 provided to the inner wall face of the holder 5 to hit the collection portion 10 of the microbe collection tool 9. Therefore, microbes M inside the collection portion 10 are eluted through the elution grooves 7 into the pure water 8 in the container 4.

Upon completion of this elution operation, the user pulls the microbe collection tool 9 upward out of the container 4.

The user then mounts the measurement chip 15 shown in FIG. 5c to a measurement chip holder 14 provided to the inner face of the front cover 2.

As shown in FIG. 5a, the measurement chip 15 in this embodiment has a chip main body 15A in the form of a long, thin plate, a measuring electrode 16, a connecting electrode 17, and a connector 18.

The measuring electrode 16 is provided on the lower end side (one end in the longitudinal direction) of the surface of the chip main body 15A, and is immersed in the pure water 8.

The connecting electrode 17 is provided on the upper end side (the other end in the longitudinal direction) of the surface of the chip main body 15A, and is connected to the measurement chip holder 14 of a measurement device.

The connector 18 connects the measuring electrode 16 and the connecting electrode 17 at the surface of the chip main body 15A.

In this embodiment, palladium is sputtered over PET (polyethylene terephthalate), which is used as the substrate of the chip main body 15A, and the palladium is worked with a laser to form the measuring electrode 16, the connecting electrode 17, and the connector 18.

In addition to palladium (Pd), the metal material of the electrodes, etc., sputtered over the PET or other substrate may be aluminum (Al), silver (Ag), gold (Au), copper (Cu), or another such metal material.

The configuration of the measurement chip 15 will be described in detail at a later point.

Figure 5:
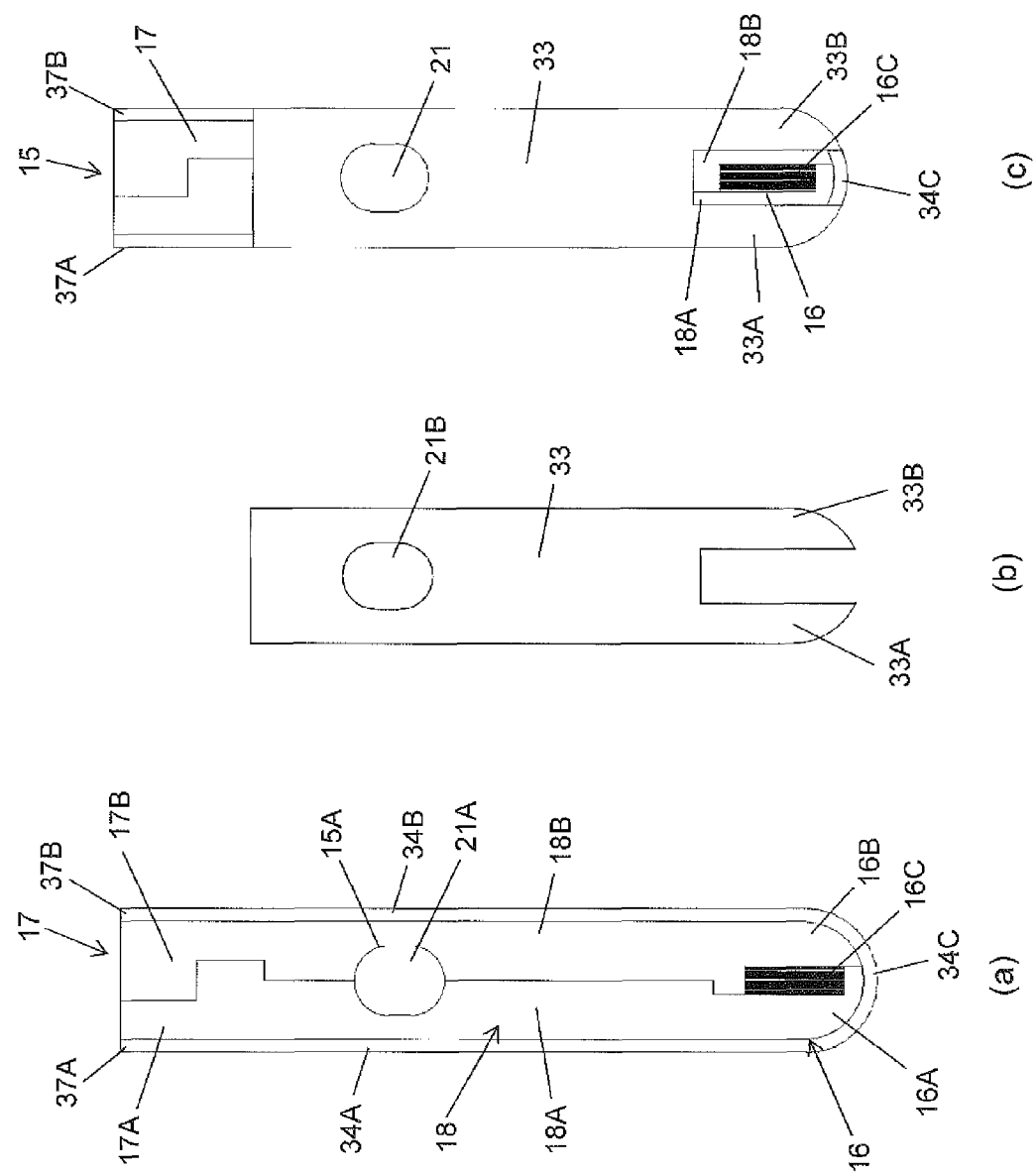
FIGS. 5a to 5c are front views of the measurement chip and the constituent members thereof in the apparatus for measuring number of microbe i FIG. 1.

Next, the user grasps the approximate middle of the measurement chip 15 in FIG. 5, and mounts the connecting electrode 17 to the measurement chip holder 14, whereupon an electrical and mechanical connection is made between the measurement chip 15 and the device as shown in FIG. 3. That is, in this embodiment, the electrode insertion portion is constituted by the front cover 2, the measurement chip holder 14, etc.

Figure 6:
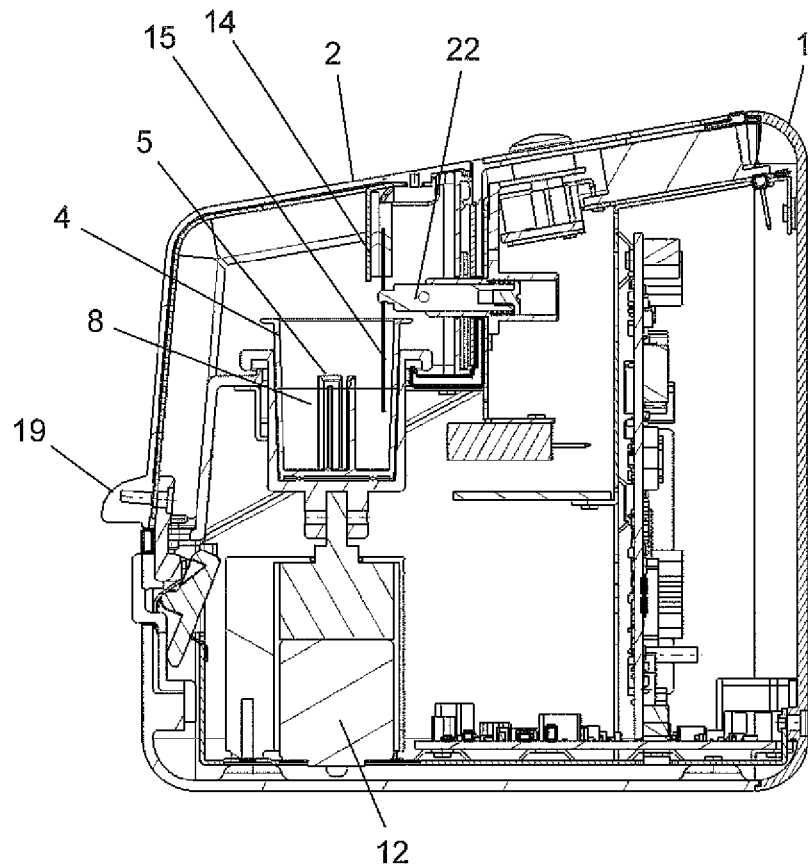
FIG. 6 is a cross section of the operating state of the apparatus for measuring number of microbe in FIG. 1.

From this state, the front cover 2 is rotated forward with a handle 19, and when it has been rotated to the state in FIG. 1, the measurement chip 15 is inserted into the container 4 via the opening in the container 4 from above the container 4 held in the container holder 3, as shown in FIG. 6. The measuring electrode 16 of the measurement chip 15 at this point is immersed in the pure water 8 in the container 4.

Next, the user presses a measurement start switch 20 (FIG. 1) to commence measurement. A voltage of 3 MHz, for example, is applied to the measuring electrode 16, and the microbes M eluted into the container 4 are gathered at the measuring electrode 16. At the same time, a voltage of 800 kHz, for example, is applied to the measuring electrode 16, and the impedance change of the measuring electrode 16 is measured to take a microbe count.

This measurement method is already known from prior publications and so forth, so it will not be described here, to keep the description from being overly complicated.

In this embodiment, the configuration is such that the motor 12 rotates the container holder 3, the container 4, and the pure water 8 during measurement, so that there are more opportunities for the microbes M that are widely diffused in the container 4 to approach the measuring electrode 16.

In a state in which a microbe count is being taken by the measurement chip 15, as shown in FIG. 6, a rod-shaped manipulator 22 is inserted into a through-hole 21 (see FIG. 5) provided in the center of the measurement chip 15.

The manipulator 22 is retracted to the rear as shown in FIG. 3 until the measurement chip 15 descends all the way in the container 4, but protrudes toward the front cover 2 as shown in FIG. 6 from immediately before the measurement chip 15 descends all the way in the container 4.

The through-hole 21 is in the form of a slot that is longer in the longitudinal direction of the measurement chip 15 (FIG. 5).

Therefore, when the user opens up the front cover 2 after measurement, the lower end of the through-hole 21 in the measurement chip 15 engages with a hook-shaped engagement component (not shown) provided to the distal end of the manipulator 22. As a result, the measurement chip 15 is separated from the measurement chip holder 14. Also, when the front cover 2 is opened up, if the front cover 2 is pulled to the rear (the right side in FIG. 6) in a state in which the measurement chip 15 has been separated from the measurement chip holder 14, the distal end of the hook-shaped engagement component (not shown) provided to the manipulator 22 comes out of the through-hole 21 in the measurement chip 15.

That is, the measurement chip 15 is pulled out of the measurement chip holder 14, and remains in the container 4 after measurement.

Accordingly, the opening of the front cover 2 does not cause the pure water 8 containing the microbes M that have adhered during measurement to inadvertently be splashed or dripped onto the front or bottom faces, etc., of the front cover 2, which is preferable in terms of cleanliness.

Figure 7:
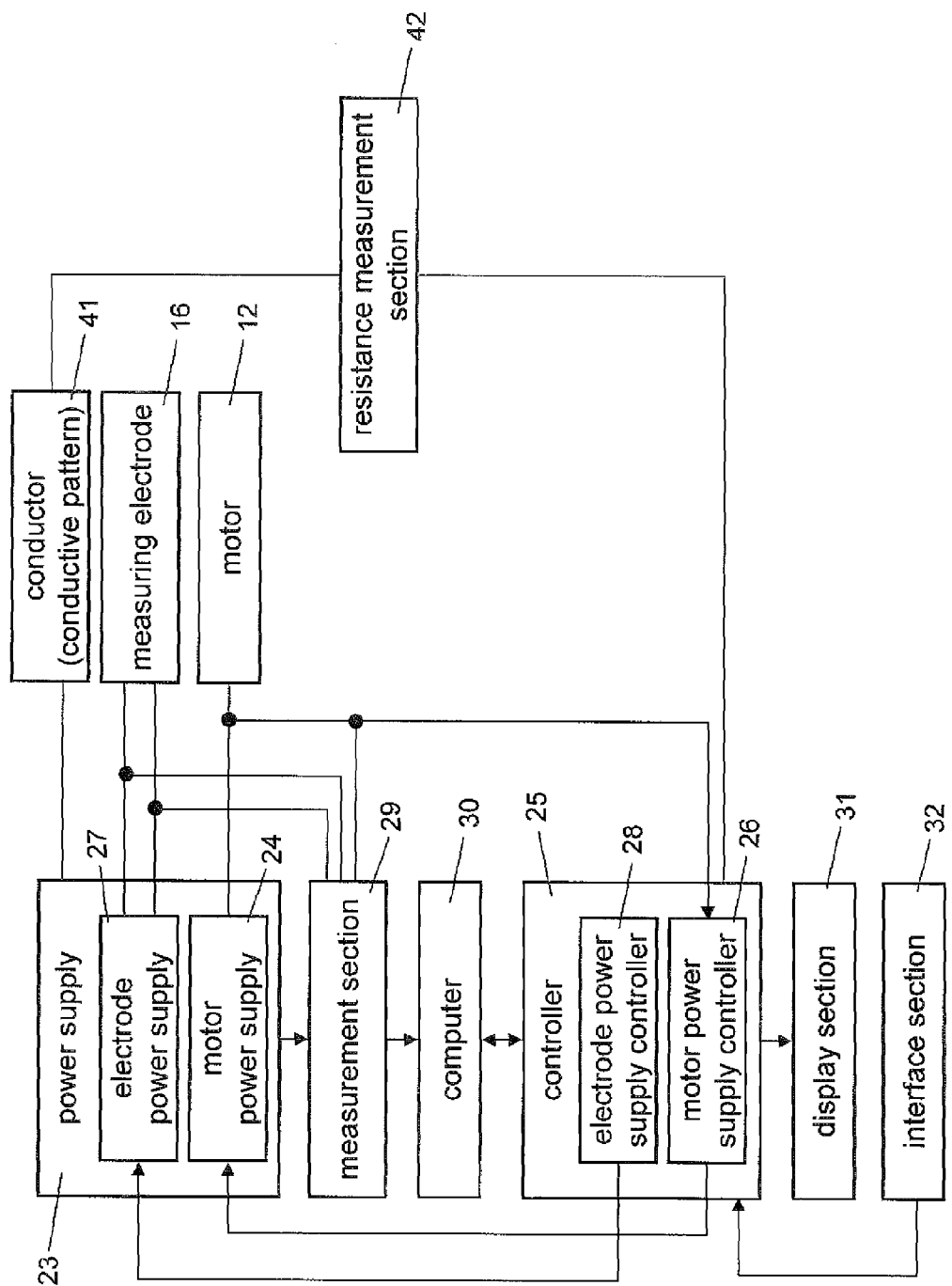
FIG. 7 is a control block diagram of the apparatus for measuring number of microbe in FIG. 1.

FIG. 7 is a control block diagram of the apparatus for measuring number of microbe used to carry out the above operation.

The motor 12 is connected to a motor power supply 24 of a power supply 23.

The motor power supply 24 is connected to a motor power supply controller 26 of the controller 25.

An electrode power supply 27 of the power supply 23 is connected to the measuring electrode 16.

The electrode power supply 27 is connected to an electrode power supply controller 28. Consequently, the above-mentioned voltages of 3 MHz and 800 kHz are applied from the electrode power supply 27 to the measuring electrode 16, and a microbe count is taken at the same time by a measurement section 29 and computer 30 connected to the measuring electrode 16. The measurement result is displayed on a display section 31 provided at the rear of the front cover 2.

An interface section 32 is used to operate the power supply. The switch 11 and operation lamp 13 shown in FIG. 2, the measurement start switch 20 in FIG. 1, and so forth are all connected to a controller 25.

Specifically, with the apparatus for measuring number of microbe in this embodiment, an electrode insertion portion (made up of the front cover 2, the measurement chip holder 14, etc.) is provided for inserting the measurement chip 15 into the container 4 through the opening in the container 4 from above the container 4 held in the container holder 3. Therefore, the container 4 can have a simple bottomed cylindrical shape having a circular opening in its upper face. As a result, the cost of producing the container 4 is lower than in the past, and measurement costs can be reduced.

Next, the relation between the pure water 8 and the measurement chip 15 during the microbe count will be described.

Figure 8:
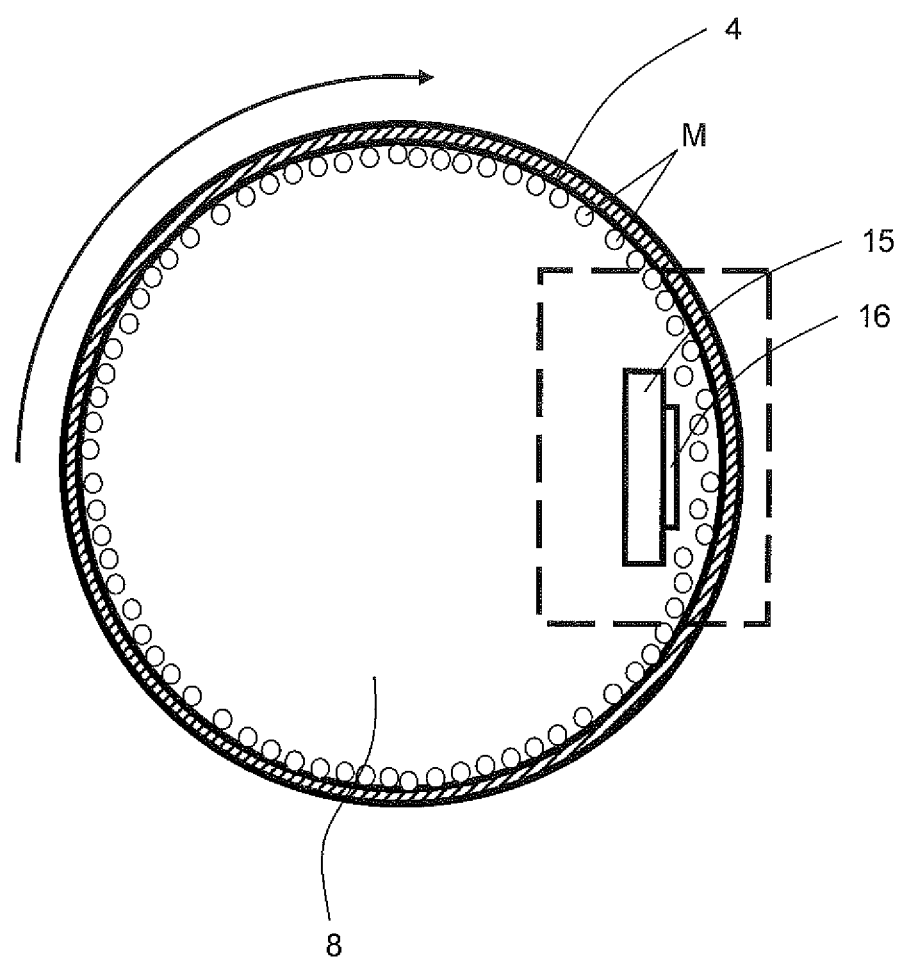
FIG. 8 is a top view of the container of the apparatus for measuring number of microbe in FIG. 1.

As shown in FIG. 8, during measurement the measurement chip 15 is disposed at a position closer to the inner wall of the container 4 than the center axis of the cylindrical container 4, and at a position that is close to the inner wall of the container 4. The measuring electrode 16 of the measurement chip 15 is disposed opposite the inner wall of the container 4.

Figure 9:
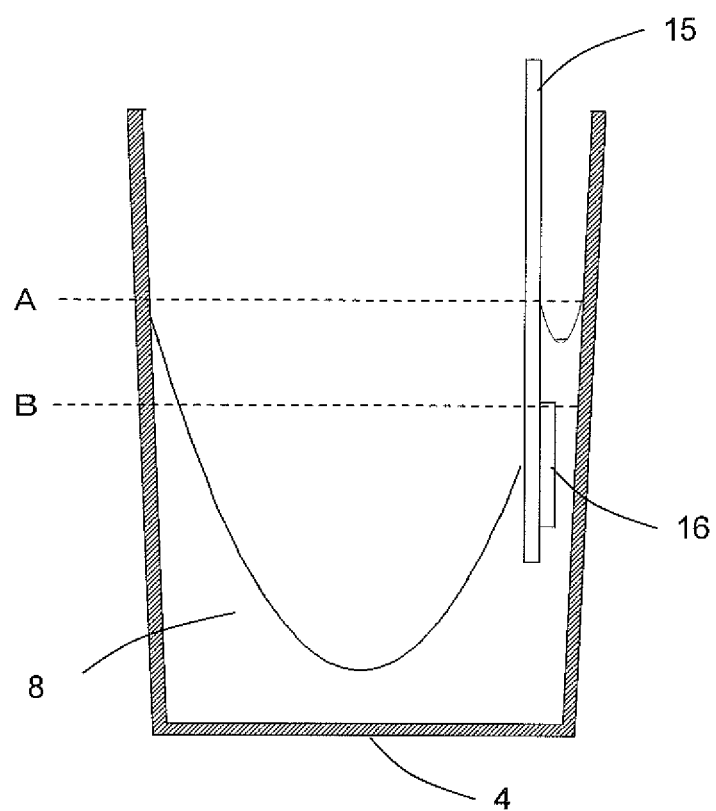
FIG. 9 is a cross section of the liquid flow inside the container of the apparatus for measuring number of microbe in FIG. 1.

In this state, when the cylindrical container 4 rotates around the center axis of the cylinder, as shown in FIG. 9, an eddy-like swirl flow is generated around the center axis running in the vertical direction in the pure water 8, and the outer peripheral portion of this swirl flow rises up to the position A in the drawing. To facilitate an understanding of this point, the holder 5 is not depicted in FIG. 9. Also, we shall assume that the level of the pure water 8 is at the position B in the drawing when the container 4 is not rotating.

Since the measurement chip 15 is disposed at a position close to the inner face of the container 4, surface tension forms a bulging portion of the pure water 8 (as shown in FIG. 9) in the portion surrounded by the measurement chip 15 and the inner wall of the container 4. This results in a state in which the measuring electrode 16 is reliably submerged in the pure water 8.

As shown in FIG. 8, the swirl flow in the container 4 subjects the microbes M contained in the pure water 8 to centrifugal force, and causes them to swirl along the inner wall of the container 4 in a state of being biased toward the inner wall of the container 4. Consequently, the microbes M swirling along the inner wall of the container 4 can be caught by the measuring electrode 16, which is disposed opposite the inner wall of the container 4.

Measuring Electrode 16

Next, the configuration of the measurement chip 15 will be described in detail through reference to FIGS. 5a to 5c.

The measurement chip 15 in this embodiment, as discussed above, comprises the measuring electrode 16, the connecting electrode 17, and the connector 18.

As shown in FIG. 5a, the measuring electrode 16 has two measuring electrodes 16A and 16B, which are opposite each other and separated by a specific gap, on the lower end side of the surface of the chip main body 15A. Because the measuring electrodes 16A and 16B are spaced apart by a specific gap, this forms a comb electrode 16C.

The connecting electrode 17 has two connecting electrodes 17A and 17B on the upper end side of the chip main body 15A.

The connector 18 has a connector 18A that connects the measuring electrode 16A and the connecting electrode 17A between the upper and lower ends of the surface of the chip main body 15A, and a connector 18B that connects the measuring electrode 16B and the connecting electrode 17B.

The measurement chip 15 in this embodiment further comprises a cover 33 (see FIG. 5b) provided in order to cover the surface of the connectors 18A and 18B between the upper and lower ends of the surface of the chip main body 15A shown in FIG. 5a.

As shown in FIG. 10b, the cover 33 is in the form of a long, thin plate, and covers substantially the entire surface of the connectors 18A and 18B. The cover 33 is formed from PET, just as the chip main body 15A is. The thickness of the cover 33 is the same as the thickness of the chip main body 15A.

This affords higher measurement accuracy of the measurement chip 15.

Specifically, as shown in FIGS. 6 and 9, the measurement chip 15 is inserted into the container 4 through the opening in the container 4 from above the container 4 held in the container holder 3. The measuring electrode 16 of the measurement chip 15 here is immersed in the pure water 8 in the container 4. The lower part of the connector 18 connected to the measuring electrode 16 is also immersed in the measurement liquid at this point. Therefore, when voltage is applied to the measuring electrode 16 at the start of measurement, voltage is also applied to this immersed part, and the immersed part has an impedance component.

When the pure water 8 is further rotated around the center axis of the container 4 for measurement, as shown in FIG. 10a, the surface of the pure water 8 is shaken by an amount L1 in the vertical direction, causing the immersed part of the connector 18 to fluctuate. This fluctuation creates variance in the impedance component of the immersed part.

The measuring electrode 16 performs measurement by a change in impedance, so variance in the impedance component of the connector 18 creates variance in the measurement value.

In view of this, in this embodiment, as discussed above, the cover 33 for covering the surface of the connectors 18A and 18B is provided between the upper and lower ends of the surface of the chip main body 15A, as shown in FIG. 10b.

Consequently, the connectors 18A and 18B do not touch the surface of the pure water 8 (that is, the shake amount L1 in the vertical direction of the liquid surface), so the connectors 18A and 18B do not have an impedance component.

Therefore, no variance of the impedance component occurs in the connectors 18A and 18B.

As a result, there is no variance in the measurement value, which means the measurement accuracy is higher.

In FIG. 10b, the connectors 18A and 18B are seen below the center of the lower end of the cover 33, and this seen part is lower than the shake amount L1 of the liquid surface. That is, the connectors 18A and 18B are parts that are always immersed in the pure water 8. Therefore, these parts are immersed and have an impedance component, but because they are always immersed, there is no variance in the impedance component.

Figure 10:
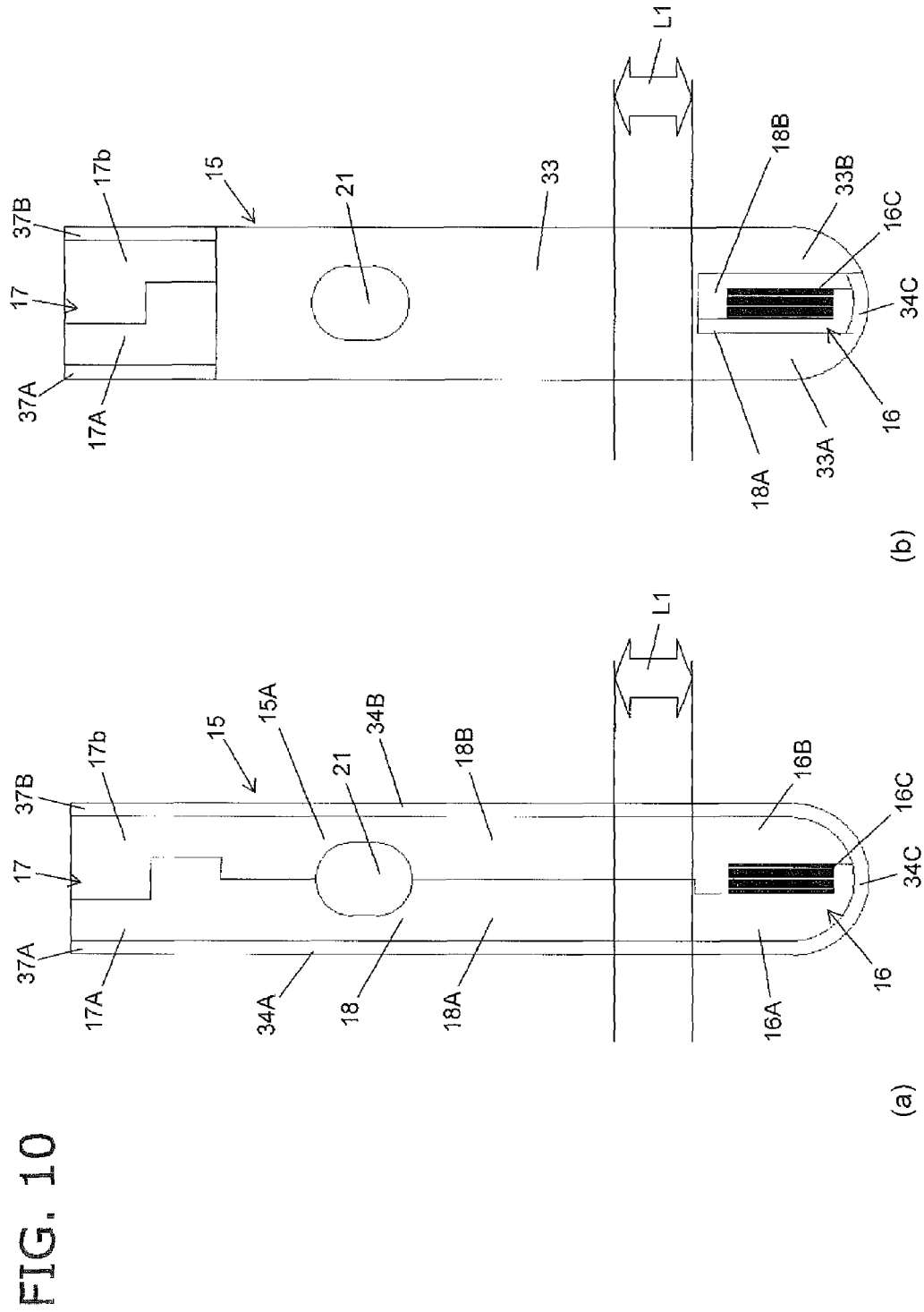
FIGS. 10a and 10b are front views of the measurement chip during operation of the apparatus for measuring number of microbe in FIG. 1.

As shown in FIG. 6, the through-hole 21 provided in the center portion of the chip main body 15A is located above the container 4 during measurement, so the liquid level does not reach the through-hole 21. That is, as shown in FIG. 10, the configuration is such that the shake amount L1 of the liquid level is produced on the connector 18 between the measuring electrode 16 and the through-hole 21.

Furthermore, in this embodiment, as shown in FIG. 10a, it is assumed that the size of the connectors 18A and 18B in the short-side direction (the width direction) is substantially the same, and is substantially one-half the width of the chip main body 15A.

Therefore, the impedance component (the direct resistance component) of the connector 18 can be reduced, and measurement sensitivity can be increased in measurement by the measuring electrode 16, which measures the microbe count from minute changes in impedance.

This point will be described in some further detail.

To accurately ascertain the change in impedance at the measuring electrode 16 (that is, a change in the microbe count), the impedance component (the direct resistance component) of the connector 18 must be reduced.

Ways to reduce the impedance component (the direct resistance component) of the connector 18 include (1) shortening the length of the connector 18 or (2) increasing the size of the connector 18 in its short-side direction (width direction), among other methods.

However, a problem with method (1) is that it is difficult to reduce the length of the connector 18 more than a certain amount because the measuring electrode 16 must be immersed in the pure water 8.1

Meanwhile, with method (2), the impedance component of the connector 18 itself does decrease when the connector 18 is made smaller in its short-side direction (width direction), but the connector 18A and connector 18B that make up the connector 18 end up being next to each other at a very close spacing. Therefore, a new impedance component is created between the immersed connector 18A and connector 18B at the portion of the connector 18 that is immersed in the pure water 8. The size of this impedance component is inversely proportional to the distance by which the connector 18A and connector 18B are separated.

That is, if the size of the connector 18 is increased in its short-side direction (width direction) in an attempt to reduce the impedance component of the connector 18, the connectors 18A and 18B will be spaced closer together. Accordingly, the impedance component generated between the immersed connector 18A and connector 18B ends up being greater.

In this embodiment, however, the cover 33 is provided to cover the surface of the connectors 18A and 18B as discussed above. Therefore, the connectors 18A and 18B are not immersed in the pure water 8, and no new impedance component is generated between the connector 18A and the connector 18B.

Accordingly, the size of the connectors 18A and 18B in the short-side direction (width direction) is substantially the same, and the impedance component (direct resistance component) of the connector 18 can be reduced by increasing the size to substantially one-half the size of the chip main body 15A in the short-side direction (width direction). This affords better measurement sensitivity of the measuring electrode 16.

Furthermore, in this embodiment, as shown in FIGS. 10a and 10b, the measuring electrodes 16A and 16B form the comb electrode 16C where they are opposite each other at a specific spacing. The comb electrode 16C is in the form of a rectangle that is longer in the longitudinal direction of the chip main body 15A, and is disposed in the center of the chip main body 15A in its short-side direction (width direction), on the lower end side of the surface of the chip main body 15A.

This is because the distance from the comb electrode 16C to the long side of the chip main body 15A opposite the comb electrode 16C is increased in the short-side direction (width direction) of the chip main body 15A. Consequently, the surface area of the two parts 16a and 16b sandwiched between the comb electrode 16C and the long side of the chip main body 15A can be increased, and the impedance component (direct resistance component) of the parts 16a and 16b can be reduced.

As a result, the impedance component (direct resistance component) of the measuring electrodes 16A and 16B of the measuring electrode 16 can be reduced, and measurement sensitivity can be improved in this respect as well.

Furthermore, in this embodiment, as shown in FIG. 10b, the cover 33 is in the form of a long plate, and the lower end center thereof is disposed more toward the upper end side of the chip main body 15A than the comb electrode 16C of the measuring electrode 16 of the chip main body 15A. Also, the lower end center of the cover 33 is disposed more toward the lower end side than the shake amount L1 of the liquid level in the vertical direction caused by rotation of the pure water 8.

Accordingly, the lower end center of the cover 33 is reliably immersed in the pure water 8. Therefore, the connectors 18A and 18B covered by the cover 33 do not touch the pure water 8, so no variance occurs in the impedance component of the connectors 18A and 18B. This results in higher measurement accuracy.

Furthermore, in this embodiment, extensions 33A and 33B are formed by extending both sides of the cover 33 on the lower end side to the lower end of the chip main body 15A. The two extensions 33A and 33B do not cover the comb electrode 16C of the measuring electrode 16 immersed in the pure water 8.

Accordingly, the comb electrode 16C of the measuring electrode 16 can be reliably brought into contact with the pure water 8, and the area around the comb electrode 16C can be reinforced by the extensions 33A and 33B. Therefore, rotation of the pure water 8 does not cause problems such as shaking of the measuring electrode 16 provided over the chip main body 15A, which is in the form of a thin, long plate, so the measurement can be carried out while the comb electrode 16C of the measuring electrode 16 is in a stable state. This also enhances measurement accuracy.

As shown in FIG. 5a, in this embodiment, a slot-form through-hole 21A is provided to the middle part of the chip main body 15A in order to separate it from the measurement device to which the chip main body 15A is mounted.

Also, as shown in FIG. 5b, the upper end of the cover 33 is disposed more on the upper end side of the chip main body 15A than the through-hole 21A of the chip main body 15A. Further, a through-hole 21B that has the same shape as the through-hole 21A is provided to the portion of the cover 33 corresponding to the through-hole 21A of the chip main body 15A. That is, the through-hole 21A and the through-hole 21B form the through-hole 21 as shown in FIG. 5c.

This makes the device easier to use for the user.

Specifically, the user opens up the front cover 2 once the measurement is complete, but as discussed above, the through-hole 21 is provided so that the measurement chip 15 will be pulled out of the measurement chip holder 14 in conjunction with this opening operation, in order to separate it into the container 4.

As shown in FIG. 5, the through-hole 21 is formed in the center portion of the measurement chip 15 (in the form of a long, thin plate) and is in the form of a slot in the longitudinal direction of the measurement chip 15. Accordingly, the portion around the through-hole 21 is weaker than the middle of the measurement chip 15. In view of this, the portion around the through-hole 21 is reinforced by disposing the upper end of the cover 33 closer to the upper end side of the chip main body 15A than the through-hole 21A of the chip main body 15A.

As discussed above, the cover 33 is similar to the chip main body 15A in that it is formed from PET, and has the same thickness as the chip main body 15A. Thus, the cover 33 has substantially the same strength as the chip main body 15A.

Consequently, during measurement, the user grasps the measurement chip 15 somewhere in its middle, and mounts the connecting electrode 17 to the measurement chip holder 14 (see FIG. 2), but since the portion around the through-hole 21 is reinforced by the cover 33, the measurement chip 15 is adequately strong for stable connection to be accomplished. This makes the device easier to use for the user, and also improves measurement accuracy.

Main Features

Conductive Patterns 34A, 34B, and 34C

The basic configuration and operation in this embodiment will be understood from the above description, and the main features of this embodiment will now be described.

As shown in FIG. 5a, ground electrodes 37A and 37B are provided at the upper end of the measurement chip 15 in this embodiment, on the outer peripheral side of the connecting electrodes 17A and 17B.

Conductive patterns 34A and 34B are provided from the ground electrodes 37A and 37B toward the measuring electrode 16 at the lower end.

The conductive patterns 34A and 34B extend from the ground electrodes 37A and 37B along the outer peripheral portion in the longitudinal direction of the measurement chip 15, and are each connected to a conductive pattern 34C.

That is, the conductive patterns 34A and 34B go past the outer peripheral side of the connectors 18A and 18B, respectively, and then are connected to the conductive pattern 34C in a state of being provided around the outer periphery of the measuring electrodes 16A and 16B.

As a result, as shown in FIG. 5a, since the conductive patterns 34A and 34B are provided around the outer periphery of the chip main body 15A in the form of a long plate, the outer periphery of the measuring electrode 16 is surrounded at the lower end of the chip main body 15A.

As described above, the measurement chip 15 is used in a state in which the chip main body 15A on shown in FIG. 5a is covered by the cover member 33 shown in FIG. 5b.

In a state in which the cover member 33 covers the chip main body 15A, as shown in FIG. 5c, the conductive pattern 34C is provided around the outer periphery of the comb electrode 16C at the lower end of the comb electrode 16C of the measuring electrode 16 that is not covered by the cover 33.

As discussed above, an electrical and mechanical connection is made when the user grasps and inserts the measurement chip 15 in FIG. 5 to mount the main body case connecting electrode 17 to the measurement chip holder 14. FIG. 11a shows the configuration of connection terminals 35A and 35B of the electrode insertion portion provided to the measurement chip holder 14.

As shown in FIG. 11a, the connection terminals 35A and 35B of the electrode insertion portion provided to the measurement chip holder 14 are respectively connected to the connecting electrodes 17A and 17B of the measurement chip 15. Ground terminals 36A and 36B provided to both sides of these connection terminals 35A and 35B are connected to the ground electrodes 37A and 37B provided to the measurement chip 15.

Of these, the ground terminal 36B is provided so as to be longer than the other connection terminals 35A and 35B and the ground terminal 36A.

Therefore, in the mounting of the measurement chip 15 to the connection terminals 35A and 35B of the electrode insertion portion, the ground terminal 36B is mounted to the ground electrode 37B of the measurement chip 15 first. Accordingly, the ground electrodes 37A and 37B of the measurement chip 15 are connected to the ground potential on the device side prior to the measuring electrode 16.

Therefore, damage to the measuring electrode 16 of the measurement chip 15 by static electricity from the user can be prevented in the mounting of the measurement chip 15 to the connection terminals 35A and 35B of the electrode insertion portion.

Specifically, with a conventional configuration, when the user holds the measurement chip in his fingers and inserts it into the electrode insertion portion of the measurement chip holder of the device in the taking of a microbe count, if the user's fingers should accidentally touch the comb electrode of the measuring electrode of the measurement chip, static electricity from the user can damage the comb electrode of the measuring electrode.

In view of this, with the measurement chip 15 in this embodiment, as discussed above, the conductive patterns 34A, 34B, and 34C, which are connected to the ground terminals 36A and 36B that serve as the ground potential of the device, are provided at the lower end of the measuring electrode 16 (although, in this embodiment, just the conductive pattern 34C is exposed from the cover member 33). This prevents the comb electrode 16C of the measuring electrode 16 from being damaged by static electricity from the user.

This point will now be described in greater detail. In this embodiment, the configuration is such that the conductive pattern 34C serves as the ground potential on the device side prior to the measuring electrode 16. Consequently, if the user accidentally touches the comb electrode 16C, he will also touch the conductive pattern 34C at the same time. As a result, static electricity from the user will flow through the conductive patterns 34C, 34A, and 34B to the device side. This prevents damage to the measuring electrode 16 by static electricity. As a result, the measurement chip 15 is easier to handle and operate.

Also, with this device, when a microbe count is taken based on a minute impedance change in the measuring electrode 16, since the measuring electrode 16, the connector 18, and the connecting electrode 17 are surrounded by the conductive patterns 34A, 34B, and 34C, the conductive patterns 34A, 34B, and 34C become barriers that reduce disturbance noise coming into the measurement chip 15.

Measuring Pure Water Temperature

In this embodiment, the structure is such that the conductive patterns 34A, 34B, and 34C are connected to the ground terminals 36A and 36B to counteract static electricity, but these conductive patterns 34A, 34B, and 34C can also be used for measuring temperature.

Figure 11:
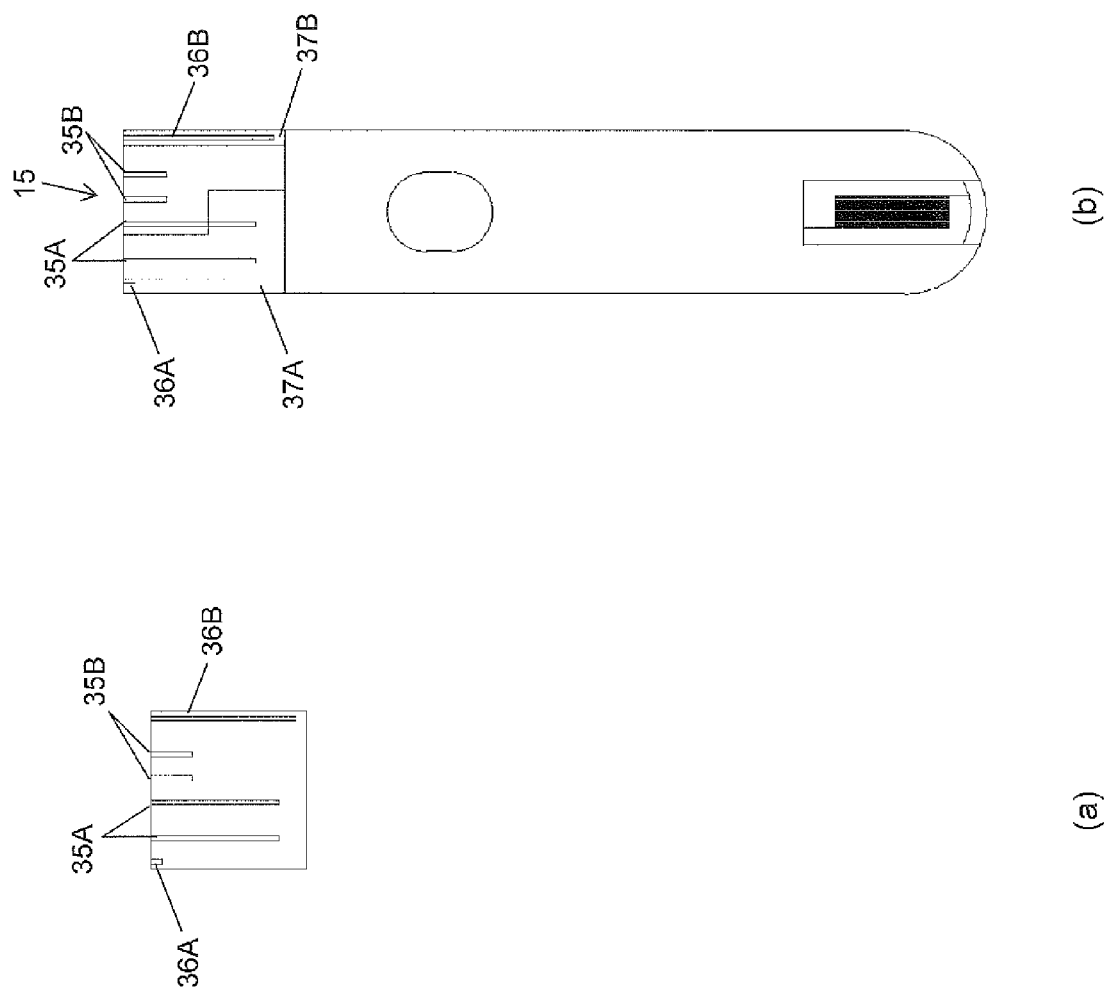
FIGS. 11a and 11b are configuration diagrams of connection terminals of the apparatus for measuring number of microbe in FIG. 1.

If the ground terminal 36A shown in FIG. 11 is a voltage application terminal, and the ground electrode 37A provided correspondingly to the measurement chip 15 is a voltage application electrode, then DC current will flow from the conductive pattern 34A to the conductive patterns 34B and 34C. As is commonly known, the resistance of a conduction path changes with temperature, so the temperature of the pure water 8 shown in FIG. 9 can be sensed by monitoring the voltage of the ground terminal 36A. Thus, this detected temperature can be used to correct the impedance between the measuring electrodes 16A and 16B that is measured.

Specifically, the temperature of the pure water 8 is affected by how many microbes have been captured between the measuring electrodes 16A and 16B, so more accurate measurement can be performed by measuring the temperature of the pure water 8 and using it to correct the impedance.

Here again, the ground terminal 36B that is used to put the conductive patterns 34A, 34B, and 34C at the ground potential is formed longer than the ground terminal 36A serving as the voltage application terminal, and the connection terminals 35A and 35B. Therefore, during mounting of the measurement chip 15, the antistatic effect discussed above can be maintained by connecting the ground terminal 36B to the conductive patterns 34A, 34B, and 34C at the very start.

That is, the conductive patterns 34A, 34B, and 34C in this case have both the function of a conductive pattern and the function of a temperature measurement pattern.

In this embodiment, the length relation of the terminals is such that ground terminal 36B>connection terminal 35A>connection terminal 35B>ground terminal 36A.

As discussed above, when the ground terminal 36A shown in FIG. 11 is the voltage application terminal, a reference resistor is connected on the current upstream side thereof, and DC current flows from this reference resistor to the ground terminal 36A, the ground electrode 37A, the conductive patterns 34A, 34B, and 34C, and the ground terminal 36B.

If the voltage between the reference resistor and the ground terminal 36A is measured, it will be possible to detect the temperature of the pure water 8 based on the change in the resistance of the conductive patterns 34A, 34B, and 34C with the temperature of the pure water 8.

The procedure for measuring the temperature of the pure water 8 with the measurement chip 15 in this embodiment will now be described in detail.

As shown in FIG. 7, a conductor 41 (the conductive patterns 34A, 34B, and 34C) is connected at its first end to the ground terminal 36A and at its second end to a resistance measurement section 42.

The resistance measurement section 42 is configured such that DC resistance can be measured in a state in which DC current is flowing to the conductive patterns 34A, 34B, and 34C.

Figure 12:
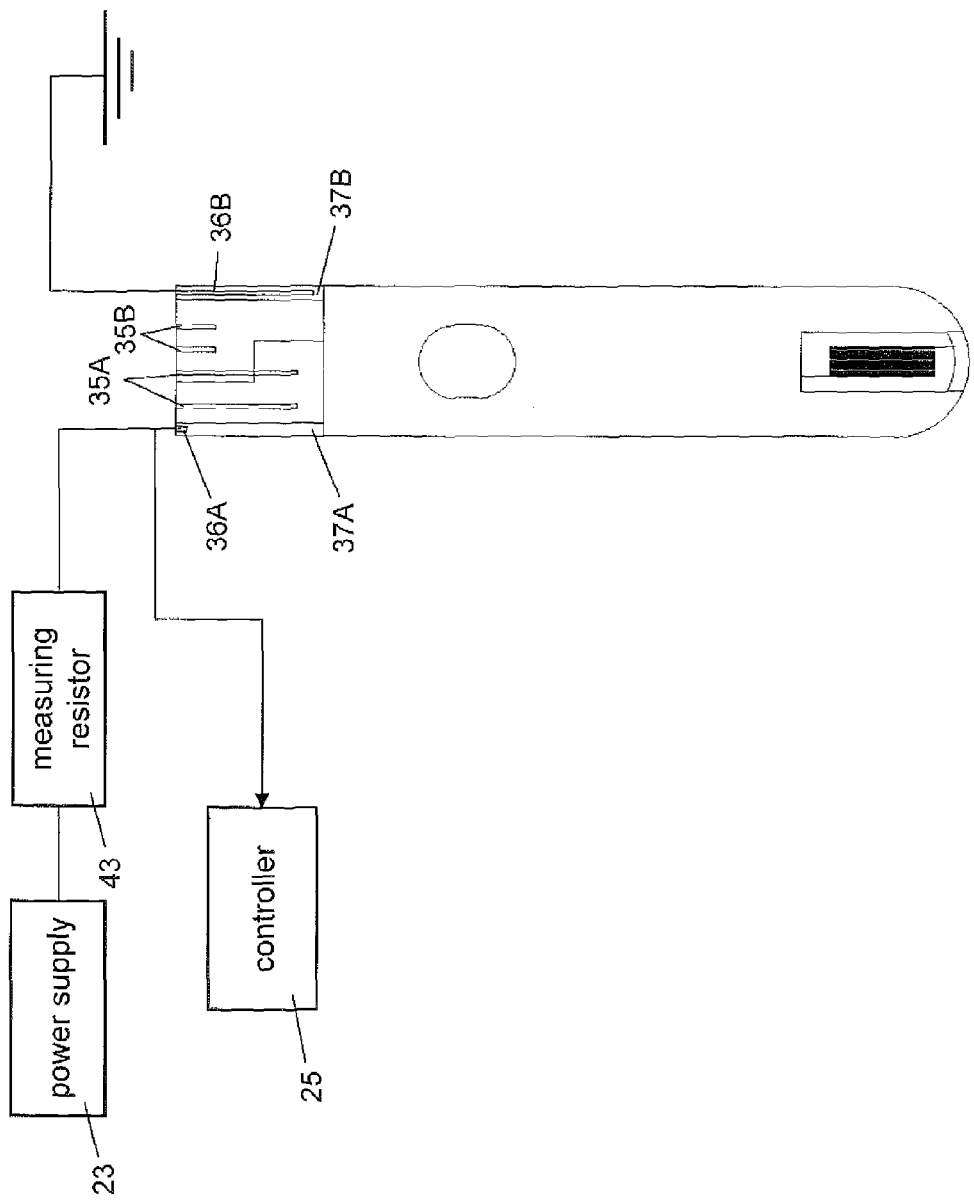
FIG. 12 shows the connection relation between the measurement chip and the apparatus for measuring number of microbe in FIG. 1.

More specifically, as shown in FIG. 12, the resistance measurement section 42 is made up of a measuring resistor 43 and the power supply 23 that is connected to this measuring resistor 43.

The terminal on the opposite side of the measuring resistor 43 from the side connected to the power supply is connected to the second end of the conductive patterns 34A, 34B, and 34C.

With this configuration, the controller 25 reads the value of the voltage at the second end of the conductive patterns 34A, 34B, and 34C, which allows the DC resistance of the conductive patterns 34A, 34B, and 34C to be detected. The temperature of analyte (the pure water 8) can be measured on the basis of this DC resistance value.

With the measurement chip 15 in this embodiment, as discussed above, palladium is used as the metal material of the electrode sputtered on a substrate such as PET. The reason for using palladium is that it offers the following advantages.

- Its resistance value or the proportional change in resistance with respect to temperature is relatively large, which makes measurement easier.
- Palladium is less susceptible to changes over time, such as oxidation.
- Since film formation and the like are easy to control in manufacture, error in the resistance value can be reduced.

Evaluation of Measurement Chip 15

With the apparatus for measuring number of microbe in this embodiment, it is possible to determine whether the measurement chip 15 has been mounted properly (and not backward), or whether or not the measurement chip 15 is a genuine product.

Specifically, with the apparatus for measuring number of microbe of this embodiment, just as in the detection of the temperature of the pure water 8 discussed above, the conduction state (such as the DC resistance state) of the conductive patterns 34A, 34B, and 34C of the measurement chip 15 inserted into the apparatus for measuring number of microbe is monitored on the device side.

Whether or not the measurement chip 15 has been properly inserted (not backward) can be detected here according to whether or not the resistance or other such detected value is within the specified range.

For instance, if the measurement chip 15 has been inserted backward, the conductive pattern will not be disposed on the rear side, so no current value (resistance value) will be detected by the controller 25 on the device side. Thus, whether or not the measurement chip 15 has been inserted properly (not backward) can be easily determined on the basis of whether or not a current value has been detected at the controller 25.

If it is determined that the measurement chip 15 has been inserted backward, this is dealt with, for example, by having the controller 25 display a message such as "chip not inserted properly" on the display section 31 provided on the front of the device. Alternatively, a warning buzzer may be sounded to alert the user to the fact that the measurement chip 15 has been inserted backward.

Also, whether or not the measurement chip 15 is a genuine product can be detected with the apparatus for measuring number of microbe in this embodiment.

Specifically, if a measurement chip that is not a genuine product is inserted, there is the possibility that the current value detected with respect to a specific applied voltage will be different from that of a genuine measurement chip 15, due to variance in quality, a difference in the composition of the metal material or the like that forms the electrodes, and so forth.

Thus, with this embodiment, whether or not the measurement chip 15 is a genuine product is determined according to whether or not the current value read at the controller 25 falls within a specific range.

If the chip is found not to be a genuine product, the controller 25 puts an error display on the display section 31 provided to the front of the device, and controls the device so that a microbe count cannot be taken. Alternatively, a warning buzzer is sounded to alert the user to the fact that proper measurement may be impossible because the measurement chip is not a genuine product.

This encourages the user to use a measurement chip 15 that is a genuine product, so that very accurate measurement can be reliably carried out.

With the chip for measuring number of microbe of the present invention, and the apparatus for measuring number of microbe used for measurement with the same, an electrode insertion portion can be provided for inserting a measurement chip through an opening into a container from above the container held by a container holder, and since this container is one having a simple bottomed cylindrical shape with an opening in the upper face, the container can be produced less expensively, and measurement costs can be lowered. Therefore, the present invention is expected to find wide application as a chip for measuring number of microbe for taking the count of microbes present in foods or in the mouth, and as an apparatus for measuring number of microbe in which this chip is used.

REFERENCE SIGNS LIST 1 main body case
2 front cover (electrode insertion portion)
3 container holder
4 container
5 holder
6 elution protrusion
7 elution groove
8 pure water (liquid)
9 microbe collection tool
10 collection portion
11 switch
12 motor
13 operation lamp
14 measurement chip holder (electrode insertion portion)
15 measurement chip
15A chip main body
16 measuring electrode
16A, 16B measuring electrode
16a, 16b part
16C comb electrode
17 connecting electrode
17A, 17B connecting electrode
18 connector
18A, 18B connector
19 handle
20 measurement start switch
21 through-hole
21A, 21B through-hole
22 manipulator
23 power supply
24 motor power supply
25 controller
26 motor power supply controller 27 electrode power supply
28 electrode power supply controller
29 measurement section
30 computer
31 display section
32 interface section
33 cover
33A, 33B extension
34, 34A, 34B, 34C conductive pattern
35, 35A, 35B connection terminal
36A, 36B ground terminal
37A, 37B ground electrode
38 measuring resistor
41 conductor (conductive pattern)
42 resistance measurement section
L1 shake amount
M microbes

The invention claimed is:

1. A chip for measuring a number of microbes, comprising:
 a chip main body in a form of a long plate;
 a measuring electrode provided on a first end side in a longitudinal direction of a surface of the chip main body, the measuring electrode being immersed in a measurement liquid and having two electrodes positioned opposite each other;
 a connecting electrode connected to the measuring electrode and provided on a second end side on an opposite side from the first end in the longitudinal direction of the surface of the chip main body;
 a ground electrode provided on the second end side of the surface of the chip main body; and
 a conductive pattern connected to the ground electrode and provided to an outer peripheral portion of the measuring electrode,
 wherein the ground electrode includes two electrodes each provided on an outer peripheral side of the connecting electrode so as to sandwich the connecting electrode.

2. The chip for a measuring number of microbes according to claim 1,
 wherein a first end of the conductive pattern is connected to the ground electrode on the second end side in the longitudinal direction of the surface of the chip main body, and
 a second end of the conductive pattern is provided around an outer periphery of the measuring electrode on the first end side in the longitudinal direction of the surface of the chip main body, and extends to the second end side in the longitudinal direction of the surface of the chip main body.

3. The chip for measuring a number of microbes according to claim 2,
 wherein the second end of the conductive pattern is provided around the outer periphery of the measuring electrode on the first end side in the longitudinal direction of the surface of the chip main body, extends to the second end side in the longitudinal direction of the surface of the chip main body, and is connected to the ground electrode provided on the second end side in the longitudinal direction of the surface of the chip main body.

4. An apparatus for measuring a number of microbes in which the chip for measuring number of microbe according to claim 3 is used, comprising:
 a container holder that holds a bottomed cylindrical container having an opening in its upper face, with the opening facing up;
 a rotary driver that rotates a liquid stored inside the container held in the container holder, around the central axis of the container running in a substantially vertical direction;
 an electrode insertion portion for inserting the chip for measuring number of microbe, through the opening in the container held in the container holder, at a position inside the container that is closer to the inner wall side than the central axis, and a position that is a specific distance away from the inner wall surface; and
 a measurement section that measures microbes at the measurement electrode of the chip for measuring number of microbe inserted into the container by the electrode insertion portion,
 wherein the electrode insertion portion has:
 a connection terminal that is connected to the connecting electrode of the chip for measuring number of microbe; and
 a ground terminal that is connected to the ground electrode of the chip for measuring number of microbe, and
 the ground terminal and the ground electrode are connected before the connection terminal and the connecting electrode are connected.

5. The apparatus for measuring a number of microbes according to claim 4,
 wherein the ground terminal of the electrode insertion portion is longer than the connection terminal.

6. The chip for measuring a number of microbes according to claim 2,
 wherein the second end of the conductive pattern is provided around the outer periphery of the measuring electrode on the first end side in the longitudinal direction of the surface of the chip main body, extends to the second end side in the longitudinal direction of the surface of the chip main body, and is connected to a voltage application electrode provided on the second end side in the longitudinal direction of the surface of the chip main body.

7. An apparatus for measuring a number of microbes in which the chip for measuring number of microbe according to claim 6 is used, comprising:
 a container holder that holds a bottomed cylindrical container having an opening in its upper face, with the opening facing up;
 a rotary driver that rotates a liquid stored inside the container held in the container holder, around the central axis of the container running in a substantially vertical direction;
 an electrode insertion portion for inserting the chip for measuring number of microbe, through the opening in the container held in the container holder, at a position inside the container that is closer to the inner wall side than the central axis, and a position that is a specific distance away from the inner wall surface; and
 a measurement section that measures microbes at the measurement electrode of the chip for measuring number of microbe inserted into the container by the electrode insertion portion,
 wherein the electrode insertion portion has:
 a connection terminal that is connected to the connecting electrode of the chip for measuring number of microbe;
 a ground terminal that is connected to the ground electrode of the chip for measuring number of microbe; and a voltage application terminal that is connected to the voltage application electrode of the chip for measuring number of microbe, and the ground terminal and the ground electrode are connected before the connection terminal and the connecting electrode are connected.

8. The apparatus for measuring a number of microbes according to claim 7, wherein the connection terminal and the connecting electrode are connected before the voltage application terminal and the voltage application electrode are connected.

9. The apparatus for measuring a number of microbes according to claim 8, wherein the ground terminal of the electrode insertion portion is longer than the connection terminal, and the connection terminal is longer than the voltage application terminal.

10. The chip for measuring a number of microbes according to claim 1, wherein the two electrodes of the measuring electrode h include mutually opposing first and second measuring electrodes on the first end side in the longitudinal direction of the surface of the chip main body, and the first and second measuring electrodes have mutually opposing comb electrodes formed a specific distance apart.

11. The chip for measuring a number of microbes according to claim 1, wherein the connection pattern that connects the connecting electrode and the measuring electrode is covered by a covering body between the first end and second end in the longitudinal direction of the surface of the chip main body.

12. An apparatus for measuring a number of microbes in which the chip for measuring number of microbe according to claim 1 is used, comprising:

a container holder that holds a bottomed cylindrical container having an opening in its upper face, with the opening facing up;

a rotary driver that rotates a liquid stored inside the container held in the container holder, around the central axis of the container running in a substantially vertical direction;

an electrode insertion portion for inserting the chip for measuring number of microbe, through the opening in the container held in the container holder, at a position inside the container that is closer to the inner wall side than the central axis, and a position that is a specific distance away from the inner wall surface; and a measurement section that measures microbes at the measurement electrode of the chip for measuring number of microbe inserted into the container by the electrode insertion portion.

* * * * *